(12) United States Patent
Kim

(10) Patent No.: US 9,398,976 B2
(45) Date of Patent: Jul. 26, 2016

(54) DRUG CARRIER DEVICE ATTACHABLE TO GLASSES

(75) Inventor: Hee Gu Kim, Gwangju (KR)

(73) Assignees: BM BIOTECHNOLOGY CO., LTD., Suncheon-Si (KR); Hee Gu Kim, Gwangju (KR)

( * ) Notice: Subject to any disclaimer, the term of this patent is extended or adjusted under 35 U.S.C. 154(b) by 512 days.

(21) Appl. No.: 13/990,578

(22) PCT Filed: Dec. 5, 2011

(86) PCT No.: PCT/KR2011/009365
§ 371 (c)(1),
(2), (4) Date: Jun. 11, 2013

(87) PCT Pub. No.: WO2012/074347
PCT Pub. Date: Jun. 7, 2012

(65) Prior Publication Data
US 2013/0253451 A1   Sep. 26, 2013

(30) Foreign Application Priority Data
Dec. 3, 2010   (KR) .......................... 10-2010-0122737

(51) Int. Cl.
*A61M 35/00* (2006.01)
*A61F 9/00* (2006.01)
*G02C 11/00* (2006.01)

(52) U.S. Cl.
CPC .............. *A61F 9/0026* (2013.01); *A61M 35/00* (2013.01); *G02C 11/00* (2013.01); *G02C 2200/02* (2013.01)

(58) Field of Classification Search
CPC .............. A61F 9/00266; A61F 9/0008; A61F 13/00063; A61F 13/124; A61F 13/00; G02C 2200/02; G02C 11/00; A61M 35/00
See application file for complete search history.

(56) References Cited

U.S. PATENT DOCUMENTS

| 4,783,163 | A | * | 11/1988 | Breault | G02C 5/126 351/136 |
| 5,907,385 | A | * | 5/1999 | Flores | G02C 3/003 351/111 |
| 7,048,372 | B1 | * | 5/2006 | Cohen | G02C 1/04 351/103 |
| 2010/0203178 | A1 | * | 8/2010 | Gupta | A61K 9/08 424/769 |
| 2010/0220175 | A1 | * | 9/2010 | Claydon | H04N 9/8715 348/43 |
| 2010/0309425 | A1 | * | 12/2010 | Zelazowski | G02C 1/08 351/138 |

FOREIGN PATENT DOCUMENTS

| JP | 2003-255280 | 9/2003 |
| KR | 20-1999-0001963 | 1/1999 |
| KR | 20-2000-0015146 | 7/2000 |
| KR | 10-2003-0066363 | 8/2003 |

* cited by examiner

*Primary Examiner* — Leslie Deak
*Assistant Examiner* — Ariana Zimbouski
(74) *Attorney, Agent, or Firm* — Lex IP Meister, PLLC

(57) ABSTRACT

Disclosed is a drug carrier device attachable to glasses, which is attached to the glasses and worn with the glasses around the eyes to enable transdermal delivery of drugs for medicinal ingredients for promoting eye fatigue recovery and improving eye diseases. The drug carrier device includes a drug carrier containing medicinal herb ingredients, and a fixing unit for detachably fixing the drug carrier on a frame of glasses. The fixing unit extends from the drug carrier and has a fixing loop whose end portion is bent to be hooked on frame of the glasses. The frame of the glasses is made of a metal to be magnetically coupled to a magnet and the fixing unit includes a permanent magnet magnetically coupled to the frame of glasses. The drug carrier device is attached to the glasses to enable drugs to penetrate into the skin around the eyes of the wearer during everyday life, thereby minimizing the cost burden associated with providing an additional pad fixing member and reducing feeling of irritation. In addition, the drug carrier device of the present invention may be attached to glasses worn at normal times, thus achieving maximized convenience of use.

9 Claims, 16 Drawing Sheets

DRUG CARRIER DEVICE ATTACHABLE TO GLASSES

TECHNICAL FIELD

The present invention relates to a drug carrier device attachable to glasses, and more particularly, to a drug carrier device attachable to glasses, which is configured to administer drug to the facial skin or mucous membranes and to have drug carriers and fixing units varying according to the type of glasses.

BACKGROUND ART

Human eyes consist of globe and optic nerves. A variety of symptoms are expressed according to the ocular diseases and disorders. There are several treatment methods of these diseases and disorders, including oral administration or direct injection into eye balls through the skin or mucous membranes. According to the oral administration, the therapeutic effects of the drug administered may decrease while pharmaceutically active ingredients of the drug pass through the liver. Accordingly, methods for directly administering the drug into the eye balls are taken into consideration.

DISCLOSURE OF THE INVENTION

In order to overcome the above-mentioned shortcomings, the present invention provides a drug carrier device attachable to glasses, which is detachably mounted on glasses to supply drug during everyday life for recovery from eye fatigue and improvement of eye diseases.

According to an aspect of the invention, there is provided a drug carrier device attachable to glasses, the drug carrier device including a drug carrier containing medicinal herb ingredients, and a fixing unit for detachably fixing the drug carrier on a frame of glasses.

The fixing unit may be a fixing loop extending from the drug carrier and may have an end portion bent to be hooked on a frame of the glasses. The frame of the glasses may be made of a metal to be magnetically coupled to a magnet and the fixing unit may include a permanent magnet magnetically coupled to the frame of glasses. The frame of the glasses may have a plurality of recessed grooves formed on a surface to which the drug carrier is attached, and the fixing unit may include fixing protrusions protruding from the drug carrier and inserted into the recessed grooves.

The drug carrier may be inclined downwards from the center toward opposite ends thereof so that it is mounted on the ridge of the wearer's nose and has a drug delivery system formed on its bottom surface, the fixing unit may upwardly extend from the drug carrier and may have a connecting loop hooked on a connection frame connecting the lens frame surrounding the lenses, and a nose pad mounting portion may be provided on the top surface of the drug carrier to mount the nose pad of the glasses.

The drug carrier may include a base frame mounted on the frame of glasses by the fixing unit, and a drug sheet detachably installed on the base frame.

As described above, according to the present invention, the drug carrier device may be attached to glasses to enable drugs to penetrate into the skin around eyes of the wearer during everyday life, thereby minimizing the cost burden associated with providing an additional pad fixing member and reducing feeling of irritation. In addition, the drug carrier device of the present invention may be attached to glasses worn at normal times, thus achieving maximized convenience of use.

BRIEF DESCRIPTION OF THE DRAWINGS

The objects, features and advantages of the present invention will be more apparent from the following detailed description in conjunction with the accompanying drawings, in which.

BEST MODE FOR CARRYING OUT THE INVENTION

Hereinafter, a drug carrier device attachable to glasses according to embodiments of the present invention will be described in detail with reference to the accompanying drawings.

Figure 1:
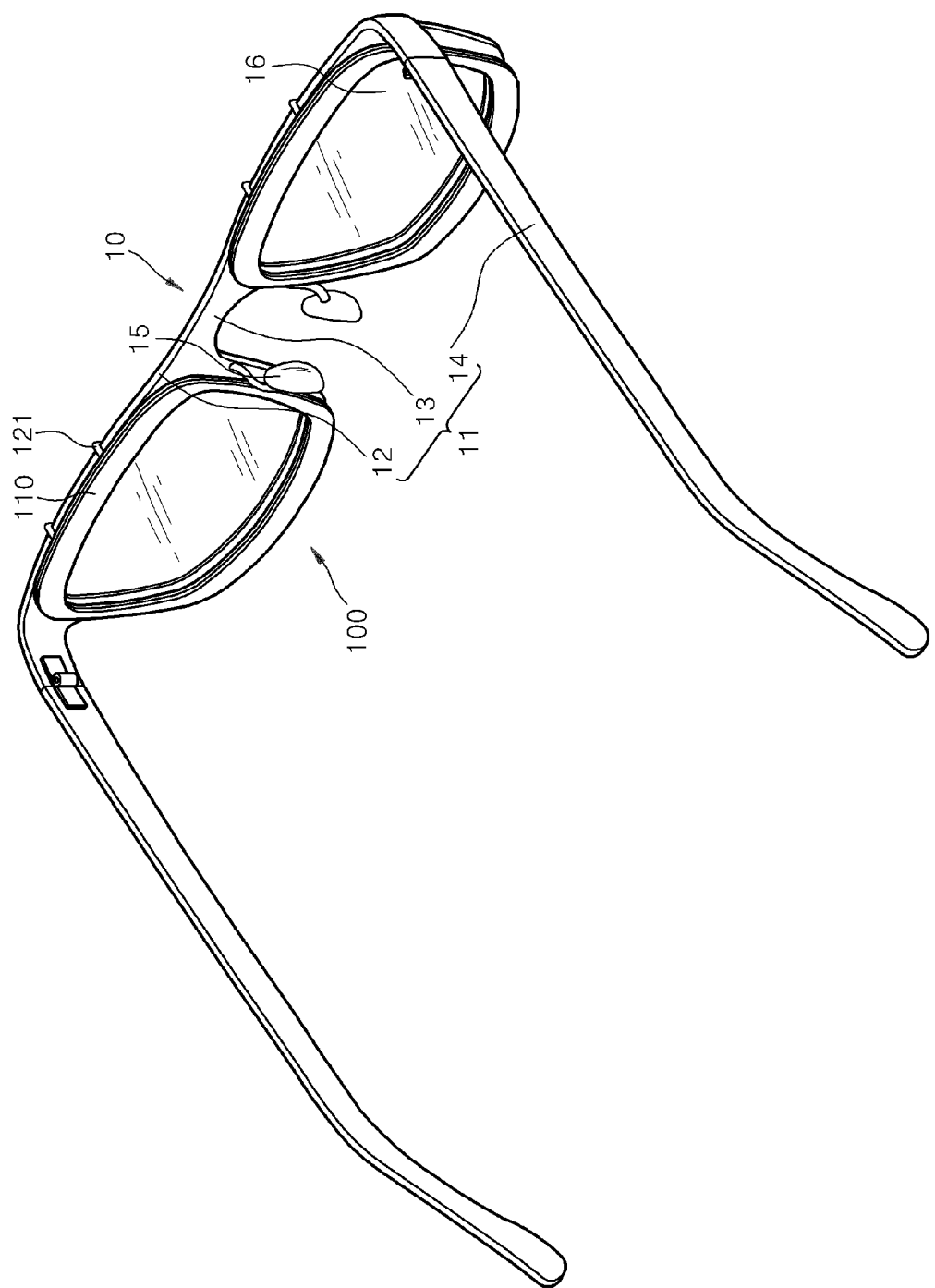
FIG. 1 is a perspective view illustrating a first embodiment of a drug carrier device attachable to glasses according to the present invention.
Figure 2:
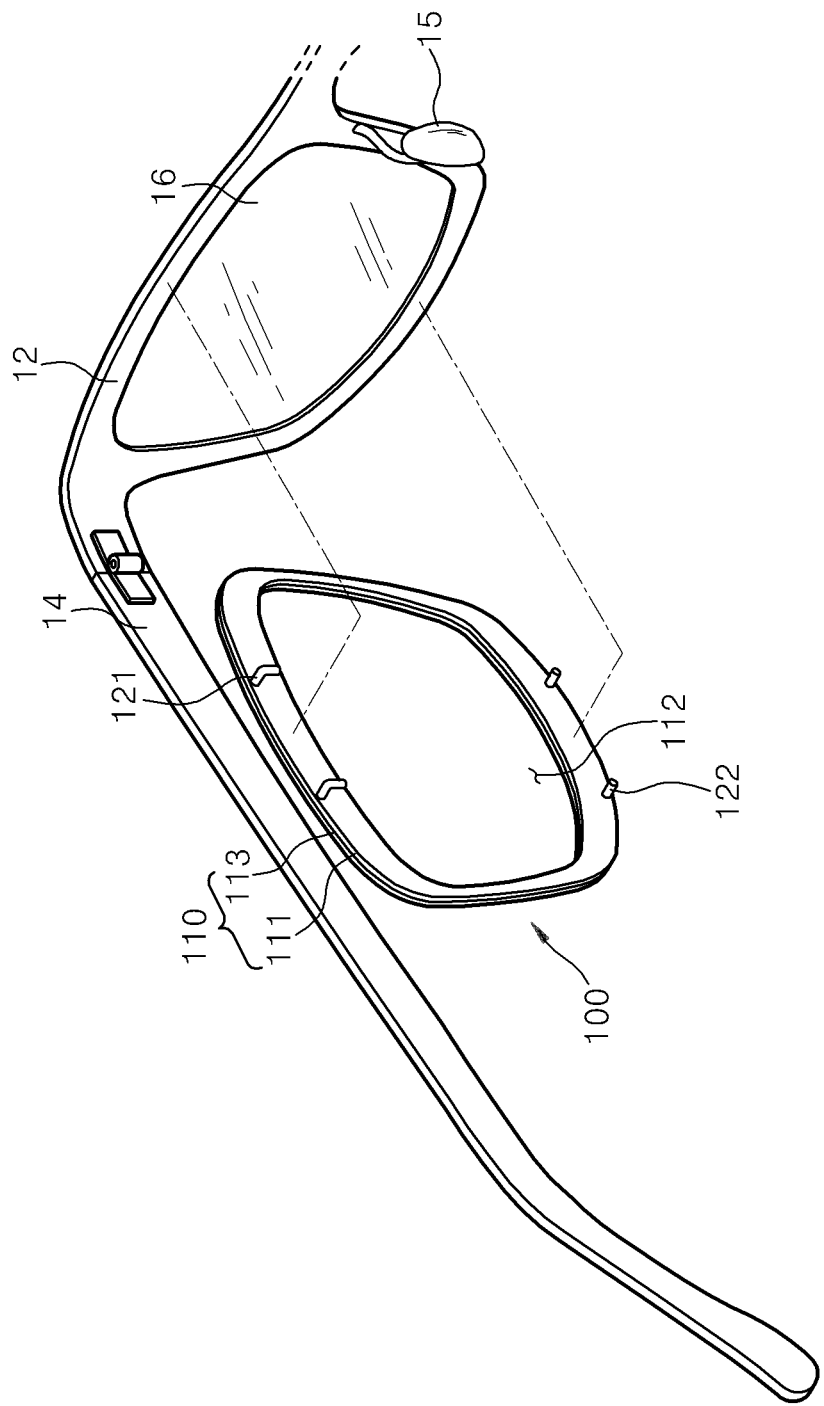
FIG. 2 is an exploded perspective view of FIG. 1.
Figure 3:
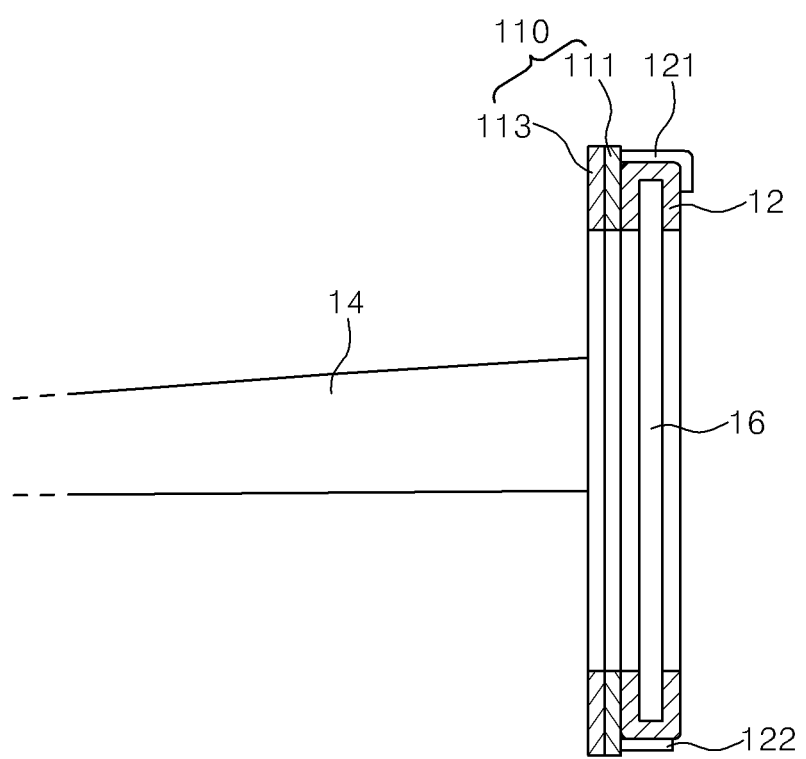
FIG. 3 is a cross-sectional view of FIG. 1.

FIGS. 1 to 3 illustrate a first embodiment of a drug carrier device 100 attachable to glasses according to the present invention. The drug carrier device 100 attachable to glasses according to the first embodiment of the present invention includes a drug carrier 110 and a fixing unit for fixing the drug carrier 110 on a frame 11 of the glasses 10.

In general, the glasses 10 include a frame 11 configured to be worn on a user's face, and lenses 16 installed on a frame 11 to protect or correct user's vision. The frame 11 includes a couple of lens frames 12 surrounding the lenses 16, a connection frame 13 connecting the lens frames 12, and a bow frame 14 extending backward from the lens frames 12 to allow its rear ends to be placed over the ears of the user. Nose pads 15 mounted on the ridge of the user's nose are formed at one side of the connection frame 13 or the lens frames 12.

The drug carrier 110 is mounted on the frame 11 through a fixing unit to supply drugs to promote eye fatigue recovery of and to improve eye diseases.

The drug carrier 110 includes a base frame 111 and a drug sheet 113 mounted on the base frame 111.

The base frame 111 is shaped of a ring having a small thickness and has view holes 112 formed at the center of the base frame 111 while passing through front and rear surfaces of the base frame 111, so that the user can see ahead while wearing the drug carrier device 100 attached to the glasses through the lenses 16.

The base frame 111 may be made of a lightweight metal material, such as aluminum, or synthetic resin or nonwoven fabric.

In the illustrated embodiment, the base frame 111 is a rectangular frame. In addition to the rectangular shape, the base frame 111 may have various shapes according to the shape of the glasses, including an elliptic or triangular shape. In addition, the base frame 111 may be selectively installed at one of upper and lower sides of the lens frames 12.

The drug sheet 113 contains a variety of medicinal ingredients including anti-oxidizing materials for promoting eye fatigue recovery or improving eye diseases.

The medicinal ingredients useful in protecting eyes from diseases and relieving eye fatigue may include lutein, zeaxanthin, melatonin, β-carotene, L-carnitine, astaxanthin, α-lipoic acid), carnosine, epigallocatechin gallate, acetyl-L-carnitine, curcumin, anthocyanin, drevogenin D, sulforaphane, carotenoids, folic acid, vitamin A, vitamin B, vitamin C, tetramethylpyrazine, fisetin, cannabinoids and vitamin E.

The above-described medicinal ingredients may be obtained by pulverizing or extracting natural medicinal herbs.

For example, lutein is contained in duckweed, semiaquilegia, grape, yellow bean, hibisci cortex, citri pericarpium, grape root, lettuce, lettuce seed, pea flower, ginko nut, rugosa rose, sunflower, sunflower root, rose of Sharon, equiseti herba, ginkgonis germen, glycinis testa, ginseng nodus and spinaciae herba. Zeaxanthin may be extracted from mori cortex, mori fructus, mori folium, persicae fructus immaturus, pruni lignum, pruni resina, pruni radix, pruni folium, pruni ramulus, pruni semen, pruni flos, citri pericarpium, ginkgonis germen, mori favilla, motherwort, lonicerae folium, lonicerae flos, equiseti herba, porpyrae siccus, pruni caulis, persicae calyx, spinaciae herba or grape.

In addition, melatonin may be extracted from petasiteae rhizoma, colocasiae rhizoma, *Colocasia esculenta* tuber or *Colocasia esculenta* folium. β-carotene may be extracted from armeniacae semen, ricini semen, glycinis semen ptisanari, citri pericarpium, whole plant of *Trichosanthes cucumeroides*, hibisci cortex, rose of Sharon, pini pollen, fici fructus, ginkgonis germen, brassicae herba, eriobotryae fructus, pini cortex, pini polium, terebinthinae oleum, brassicae herba, glycinis testa, hirundinis nidus, fucus cum caesalpiniae, fucus cum carthami, lettuce, lettuce seed, pea flower, *Trichosanthes cucumeroides* semen, *Colocasia esculenta* tuber, porpyrae siccus, melo pediculus, persicae fructus immaturus, raphani radix, semiaquilegia, sunflower, sunflower root, eriobotryae folium, pruni lignum, pruni resina, pruni radix, pruni caulis, pruni folium, pruni ramulus, pruni semen, pruni flos, glycine semen nigrae, spinaciae herba, tuberous root of *Trichosanthes cucumeroides, Trichosanthes cucumeroides* radix, juniperi favilla, *Colocasia esculenta* folium, ginko nut, persicae calyx, ricini folium, carthami flos, carthami novella, rugosa rose, lonicerae folium, lonicerae flos, trigonellae semen, verbenae herba, equiseti herba, carthami semen or yellow bean.

Curcumin may be extracted from curcumae radix or *Curcuma longa* rhizoma, folic acid may be extracted from apis nidus, mali fructus, *Angelica sinensis* radix, honey, ginseng nodus or ginseng, vitamin $B_1$ may be extracted from acanthopanacis cortex, hordei fructus germinatus, wild honey, auriculariae polyporus, phragmitis folium, toonae folium, toonae radicis cortex, massa medicata fermentata, ricini folium, phragmitis rhizoma, porpyrae siccus, phragmitis favilla or ricini semen, and vitamin C may be extracted from *Allium fistulosum*, capsellae semen, capsellae herba, coprini herba, *Citrus unshiu* immature peel, toonae folium, *Colocasia esculenta* rhizoma, amaranthi semen, lycii radicis cortex, cyperi rhizoma, trigonellae semen, perillae folium, allii bulbus, sanguisorbae radix, cnidii rhizoma, *Acorus calamus* rhizoma, papaveris fructus pericarpium, portulacea herba, raphani radix, foeniculi fructus, raphani semen, cnidii surculus, porpyrae siccus, cassiae folium, ixertis herba, lasiosphaera seu calvatia, sacchari tuber or lycii fructus. The medicinal ingredients useful for protecting eyes from diseases and relieving eye fatigue may be extracted from these medicinal herbs.

In addition, the drug sheet 113 may include medicinal herb ingredients prepared by pulverizing or extracting at least one medicinal herb selected from duckweed, semiaquilegia, grape, yellow bean, hibisci cortex, citri pericarpium, grape root, lettuce, lettuce seed, pea flower, ginko nut, rugosa rose, sunflower, sunflower root, rose of Sharon, equiseti herba, ginkgonis germen, glycinis testa, ginseng nodus, spinaciae herba, mori cortex, mori fructus, mori folium, persicae fructus immaturus, pruni lignum, pruni resina, pruni radix, pruni folium, pruni ramulus, pruni semen, pruni flos, mori favilla, motherwort, lonicerae folium, lonicerae flos, porpyrae siccus, pruni caulis, persicae calyx, petasiteae rhizoma, colocasiae rhizoma, *Colocasia esculenta* tuber, *Colocasia esculenta* folium, armeniacae semen, ricini semen, glycinis semen ptisanari, whole plant of *Trichosanthes cucumeroides*, pini pollen, fici fructus, brassicae herba, eriobotryae fructus, pini cortex, pini polium, terebinthinae oleum, brassicae herba, hirundinis nidus, fucus cum caesalpiniae, fucus cum carthami, *Trichosanthes cucumeroides* semen, melo pediculus, raphani radix, glycine semen nigrae, tuberous root of *Trichosanthes cucumeroides, Trichosanthes cucumeroides* radix, juniperi favilla, ricini folium, carthami flos, carthami novella, trigonellae semen, verbenae herba, carthami semen, curcumae radix, *Curcuma longa* rhizoma, apis nidus, mali fructus, *Angelica sinensis* radix, honey, ginseng, acanthopanacis cortex, hordei fructus germinatus, wild honey, auriculariae polyporus, phragmitis folium, toonae folium, toonae radicis cortex, massa medicata fermentata, phragmitis rhizoma, phragmitis favilla, *Allium fistulosum*, capsellae semen, capsellae herba, coprini herba, *Citrus unshiu* immature peel, *Colocasia esculenta* rhizoma, amaranthi semen, lycii radicis cortex, cyperi rhizoma, perillae folium, allii bulbus, sanguisorbae radix, cnidii rhizoma, *Acorus calamus* rhizoma, papaveris fructus pericarpium, portulacea herba, foeniculi fructus, raphani semen, cnidii surculus, cassiae folium, ixertis herba, lasiosphaera seu calvatia, sacchari tuber, lycii fructus, asparagi radix, liriopes radix, rehmanniae radix, rehmanniae radix preparata, white ginseng, mint, tangerine, sweet potato, poria, dioscoreae rhizoma, achyranthis radix, dendrobii herba, cassiae semen, chrysanthemum, cuscutae semen, aurantii fructus pericarpium, gazellae cornu, saposhnikovia radix, celosiae semen, schizandrae fructus, glycyrrhizae radix, coptidis rhizoma, tribuli fructus, ligustici rhizoma, chrysanthemum, equiseti herba, osterici radix, viticis fructus, glycyrrhizae radix preparata, gypsum, scutellariae radix, forsythiae fructus, moutan cortex, alismatis rhizoma, corni fructus, marigold, tribuli fructus, angelicae gigantis radix, hirudonis caro, cicadae periostracum, bupleuri radix, cimicifugae rhizoma, ginseng, clematidis radix, anemarrhenae rhizoma, citri pericarpium, atractylodis rhizoma, scrophulariae radix, *Angelica pubescens* radix, carthami semen, acanthopanacis cortex, sophorae radix, thujae resina, *Polygonum multiflorum* radix, astragali radix, schizonepetae spica, fingered citron, banana, mushroom, blueberry, green coffee berry, green tea, kale, carrot, spinach, lettuce, pumpkin and broccoli.

In addition to the medicinal herb ingredients, other medicinal herb ingredients may be acquired from at least one medicinal herb selected from chrysanthemum, lemon, orange, cherry, pomegranate, grape, strawberry, rose, lilac, acacia, freesia, lily, lavender, mint, jasmine, mugwort, rosemary, pine, flavonoid, fir, coffee, ginseng, fingered citron, chamomile, cypress, geranium, juniper, roseclary, sage, lime, neroli, sandalwood bergamot, eucalyptus, lime neroli, peppermint, ylang-ylang, patchouli, myrrh, frankincense, cedarwood, and sandalwood.

The medicinal herb ingredients extracted from the medicinal herbs are liquefied, gelled to form the drug sheet 113 in the form of a capsule or a pad. Thereafter, the drug sheet 113 is combined with the base frame 111 and positioned around the eyes. Then, since the medicinal herb ingredients discharged from the drug sheet 113 penetrate into the interior of the body through the skin around the eyes, eye fatigue recovery and eye disease improvement can be achieved by the medicinal herb ingredients.

The drug sheet 113 is detachably coupled to base frame 111, thereby allowing the base frame 111 to be repeatedly used, minimizing the replacement cost of the drug sheet 113 by replacing only the drug sheet 113, and selectively employing a variety of medicinal herb ingredients according to the purpose of using the drug sheet 113 and personal preference of the user.

As described above, the fixing unit fixes the drug carrier 110 to the lens frames 12 of the glasses 10.

In the illustrated embodiment, the fixing unit includes upper fixing loops 121 and lower fixing loops 122. The upper fixing loops 121 protrude at upper ends of a front surface of the base frame 111, and the lower fixing loops 122 protrude at lower ends of the front surface of the base frame 111.

Each of the upper fixing loops 121 has a downwardly bent end, and each of the lower fixing loops 122 has only to support lower portions of the lens frames 12 so that it protrudes frontwards a predetermined length. The lower fixing loops 122 may also be configured such that ends thereof are upwardly bent.

In the illustrated embodiment, the drug carrier device 100 attachable to glasses is configured such that the upper fixing loops 121 are installed to be hooked on the lens frames 12 of the glasses 10 and the base frame 111 having the drug sheet 113 attached thereto is attached to the glasses 10. Thereafter, if the glasses 10 are worn, the medicinal herb ingredients contained in the drug carrier 110 penetrate into the interior of the body through the skin around the eyes, thereby demonstrating pharmacological efficacy.

In the illustrated embodiment, the fixing unit is configured such that fixing loops are hooked on the lens frames 12 to achieve a fixing function. However, the fixing loops may also be configured to be hooked not only on the lens frames 12 but also on the bow frame 14 or the connection frame 13 to fix the drug carrier 110 to the glasses 10. In a case where the glasses 10 are rimless glasses, since the connection frame 13 or the bow frame 14 is directly coupled to the lenses 16, the fixing loops may be configured to be hooked on upper and lower portions of the lenses 16.

Figure 9:
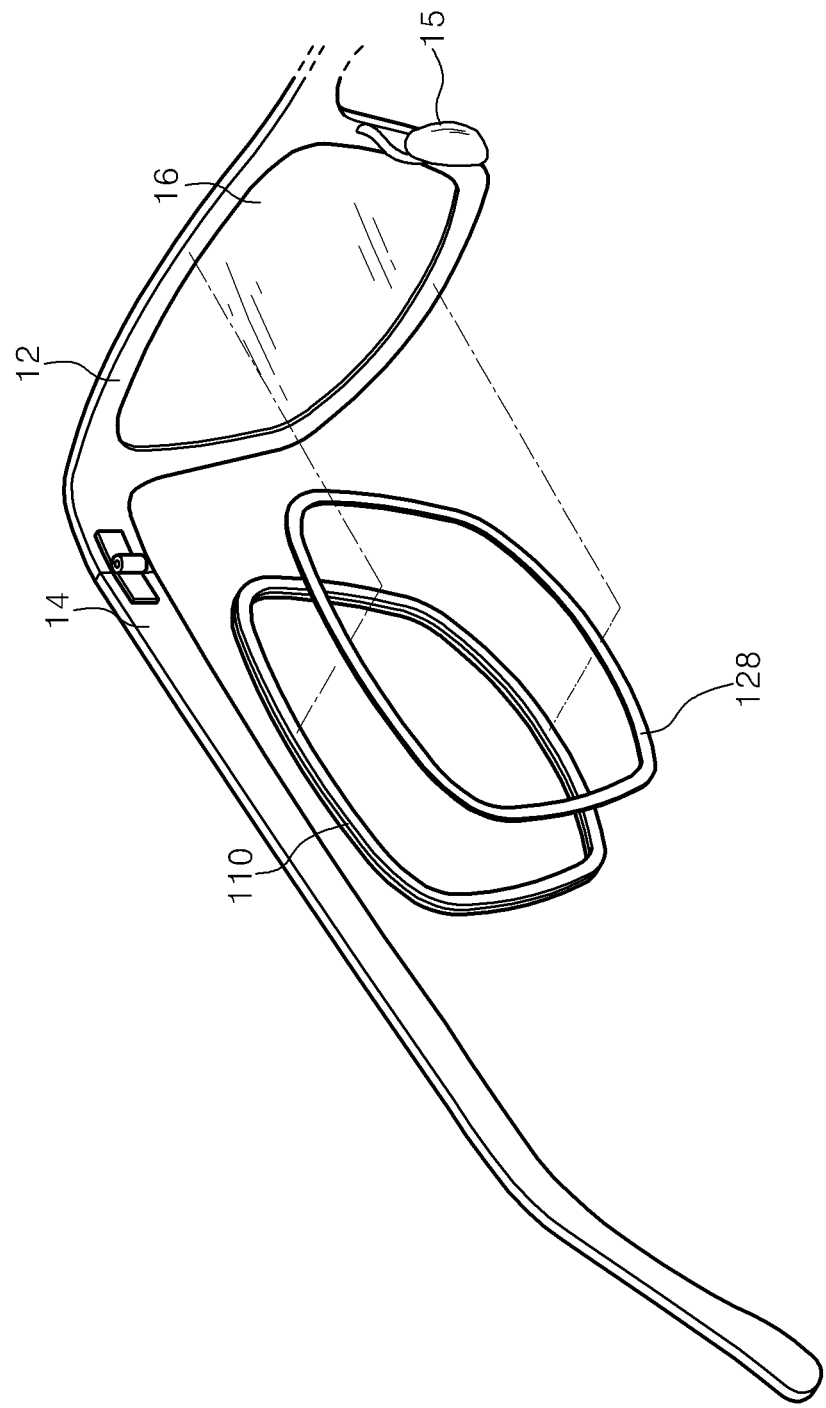
FIG. 9 is an exploded perspective view of a drug carrier device attachable to glasses including a fixing unit using an adhesive sheet.

In addition, the drug carrier 110 may be formed by coating an adhesive material on the base frame 111 or may be directly attached to the glasses 1 by an adhesive sheet 128 containing an adhesive material, as shown in FIG. 9.

Figure 4:
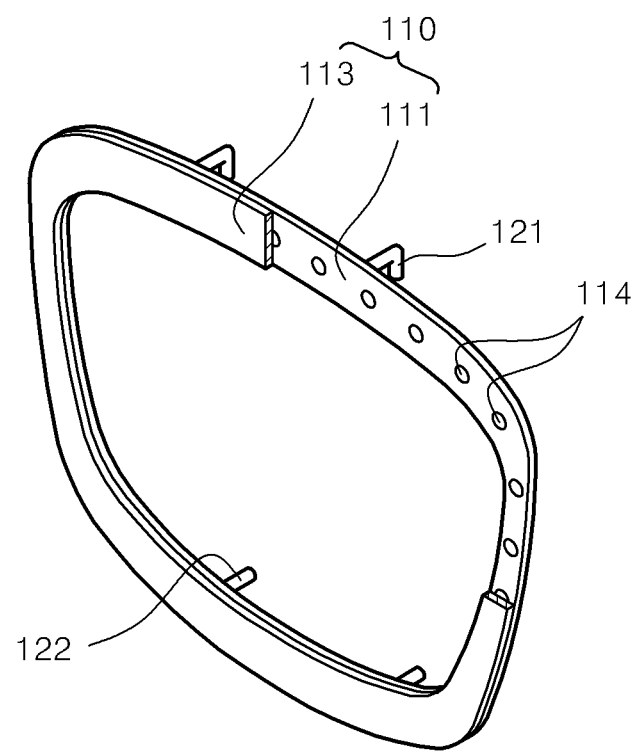
FIG. 4 is a partially cut-away perspective view illustrating another embodiment in which a magnet is attached to a base frame.

In addition, as shown in FIG. 4, a magnet may be mounted on a surface of the base frame 111 to which the drug sheet 113 is attached, thereby activating molecular motions of the medicinal herb ingredients contained in the drug sheet 113 and minimizing EMI of an electronic product emitting electromagnetic waves, such as a variety of display devices, including a 3D TV, a monitor, and so on.

Figure 5:
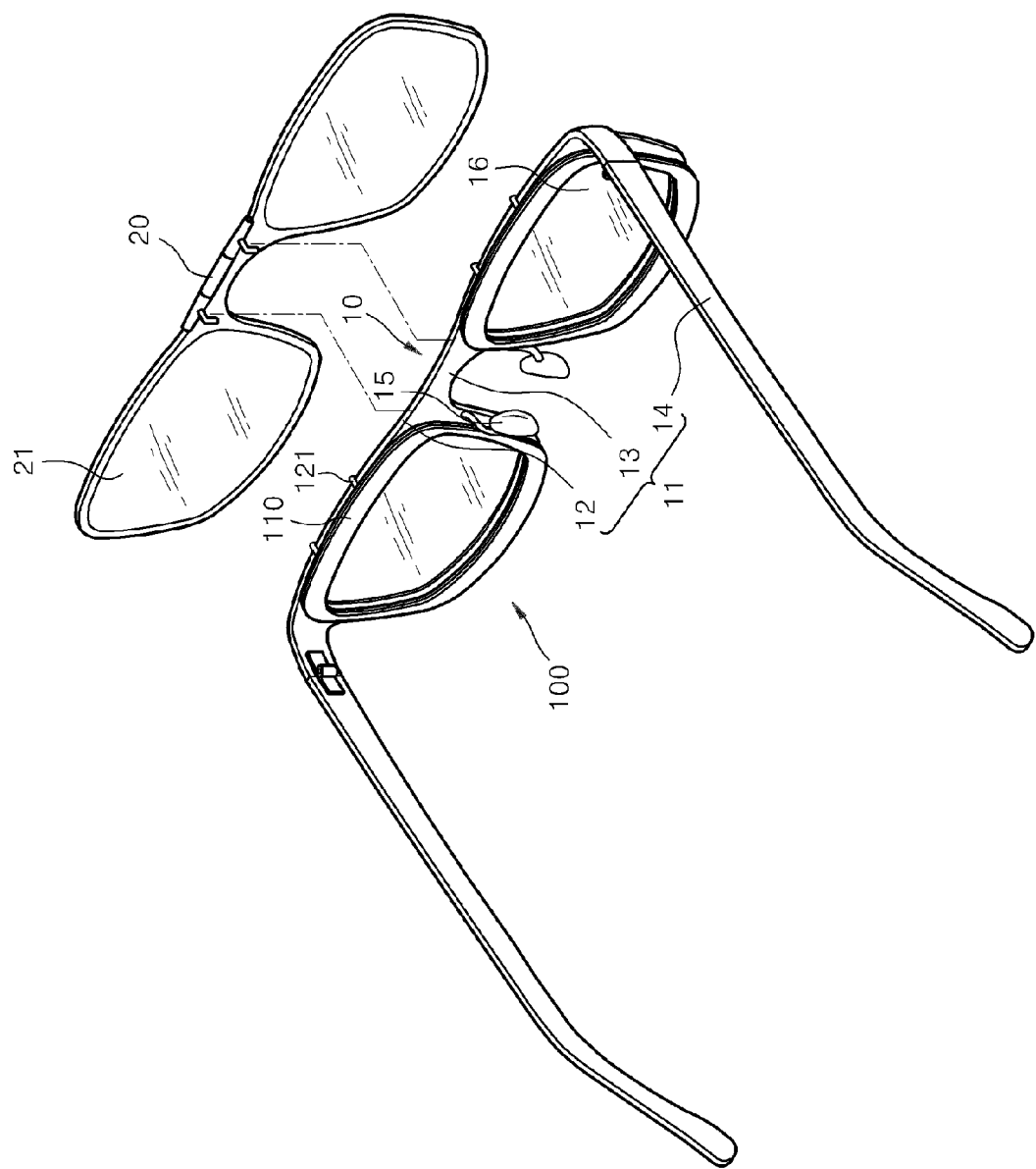
FIG. 5 is an exploded perspective view illustrating an embodiment in which an auxiliary lens frame including a polarizing lens is further provided in front of glasses.

As the lens 16, a vision correcting lens or a vision protecting lens may be employed. Alternatively, a polarizing lens may be employed to watch a 3D TV. In addition, as shown in FIG. 5, an ordinary lens may also be used as the lens 16, and an auxiliary lens frame 20 having a polarizing lens 21 may further be provided in front of the lens frames 12.

Figure 6:
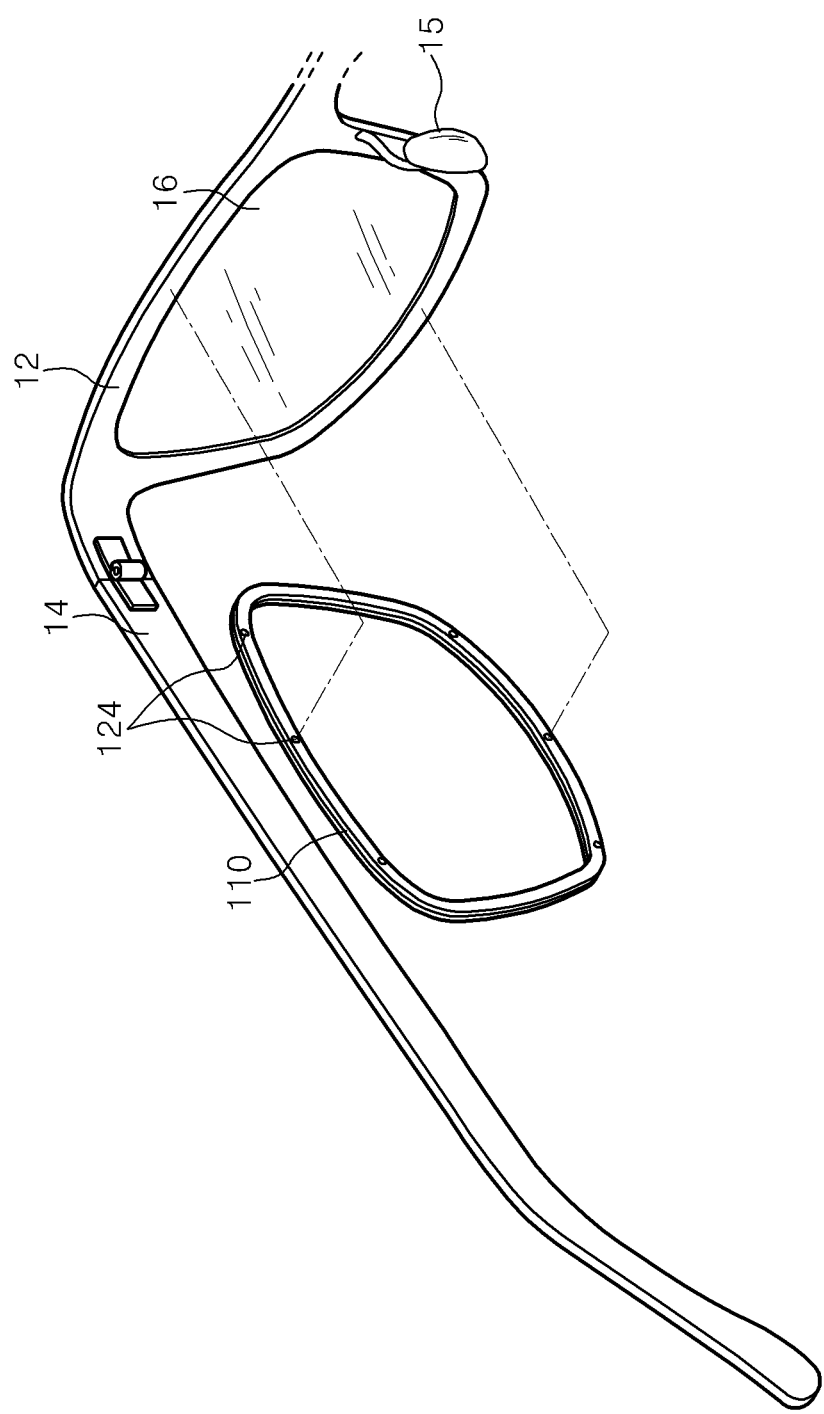
FIG. 6 is a perspective view illustrating a second embodiment of a drug carrier device attachable to glasses according to the present invention.

FIG. 6 illustrates an embodiment of the drug carrier device in which a permanent magnet is used as a fixing unit.

In the illustrated embodiment, permanent magnet pieces 124 are installed on the base frame 111 on a front surface making contact with a lens frame 12.

In the illustrated embodiment, the glasses 10 include a frame 11 made of a metal that is a magnetic material, and the base frame 111 are detachably coupled to the glasses 10 to be magnetically coupled to the glasses 10 through the permanent magnet pieces 124 installed on the base frame 111.

In the illustrated embodiment, the fixing unit may also be formed by coupling the permanent magnet pieces 124 to the base frame 111 made of a metal or a synthetic resin. Alternatively, the base frame 111 itself may be formed of a permanent magnet having a magnetic property.

Figure 7:
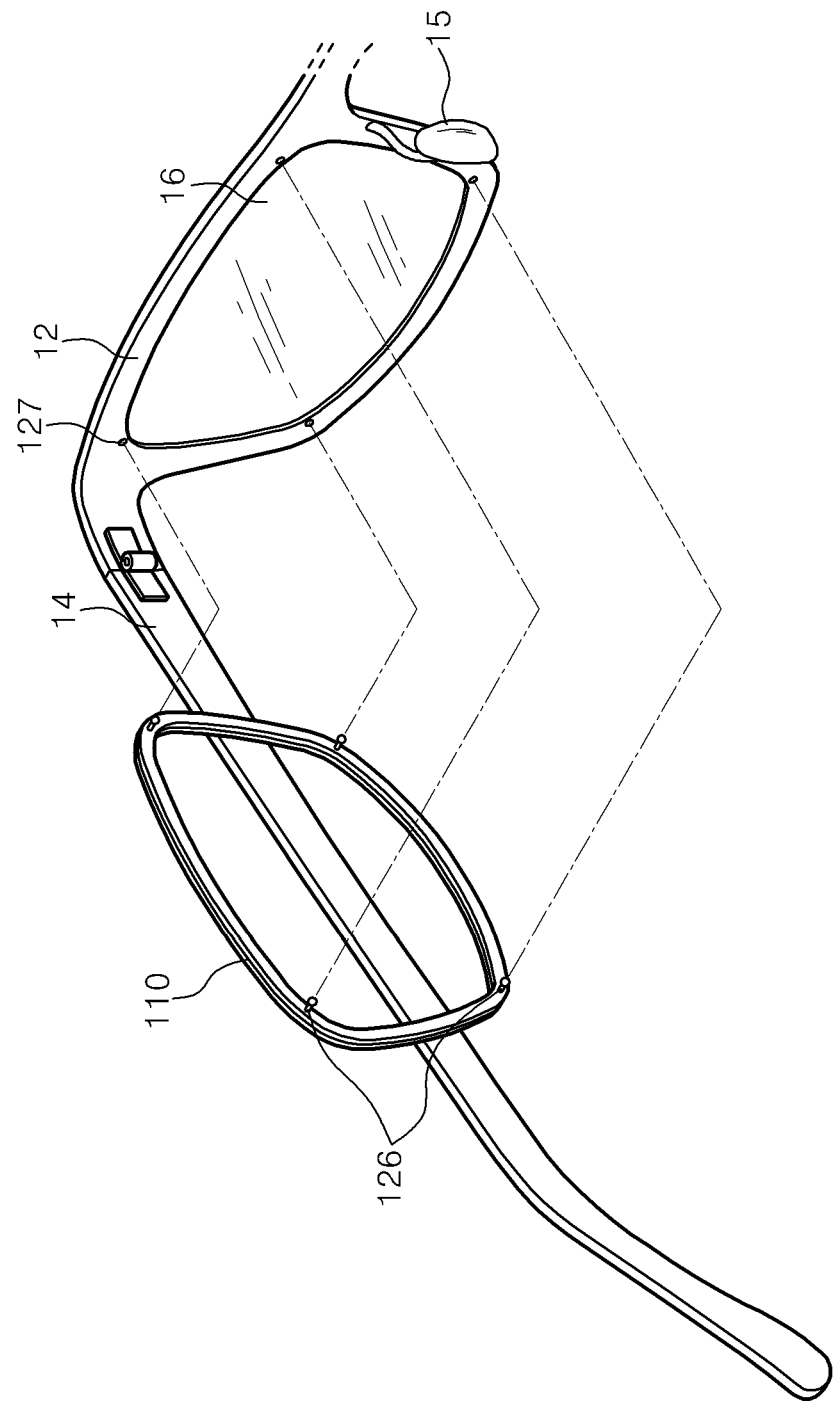
FIG. 7 is a perspective view illustrating a third embodiment of a drug carrier device attachable to glasses according to the present invention.

Referring to FIG. 7, the fixing unit may include fixing protrusions 126 protruding from the base frame 111.

Fixing grooves 127 are formed on the inner surface of a lens frames 12 facing a facial surface of a user, and fixing protrusions 126 are formed on a front surface of the base frame 111 to be engaged with the fixing grooves 127. In such a manner, the fixing protrusions 126 are inserted into the fixing grooves 127, thereby fixing the drug carrier 110 to glasses 10.

In the above-described embodiments, the drug carrier 110 is fixed on the frame of the glasses 10 to supply medicinal ingredients to portions around the user's eyes.

Figure 8:
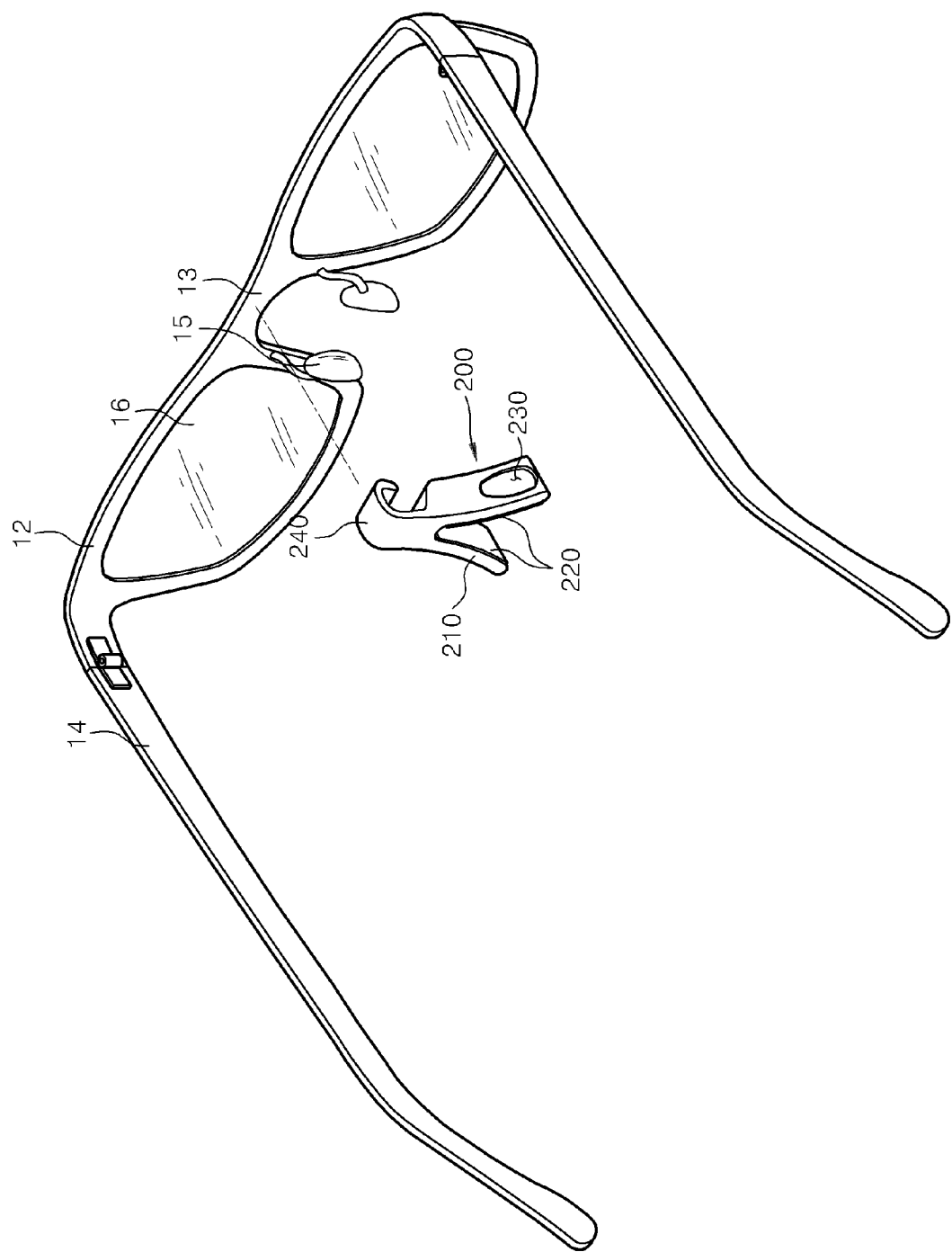
FIG. 8 is a perspective view illustrating a fourth embodiment of a drug carrier device attachable to glasses according to the present invention.

FIG. 8 is a perspective view illustrating a fourth embodiment of a drug carrier device 200 attachable to glasses according to the present invention.

Referring to FIG. 8, the drug carrier device 200 attachable to glasses 10 includes a drug carrier 210 mounted on the ridge of the user's nose and a fixing unit for fixing the drug carrier 210 to the glasses 10.

The drug carrier 210 includes a drug sheet 220 inclined downwards from the center toward opposite ends thereof, that is, in an inverted 'V' shape and containing drugs on its bottom surface.

The drug carrier device 200 according to the illustrated embodiment is mounted on the ridge of the nose to induce penetration of medicinal ingredients capable of improving nasal diseases, such as nasal inflammation or nasal congestion. The medicinal herb ingredients contained in the drug sheet 220 may be prepared by extracting and stirring medicinal herbs, such as lotus root, elm bark, *Houttuynia cordata* root, Flos Lonicerae, etc., which are helpful in relieving nasal inflammation or nasal congestion.

The fixing unit is formed of a connecting loop 240 upwardly extending from the center of a top surface of the drug carrier 210 and hooked on a connection frame 13 of the glasses 1, and a nose pad mounting portion 230 is provided on the top surface of the drug carrier 210 to mount a nose pad 15 of the glasses 10, thereby allowing the drug carrier 210 to serve as the nose pad 15 of the glasses 10.

Figure 11:
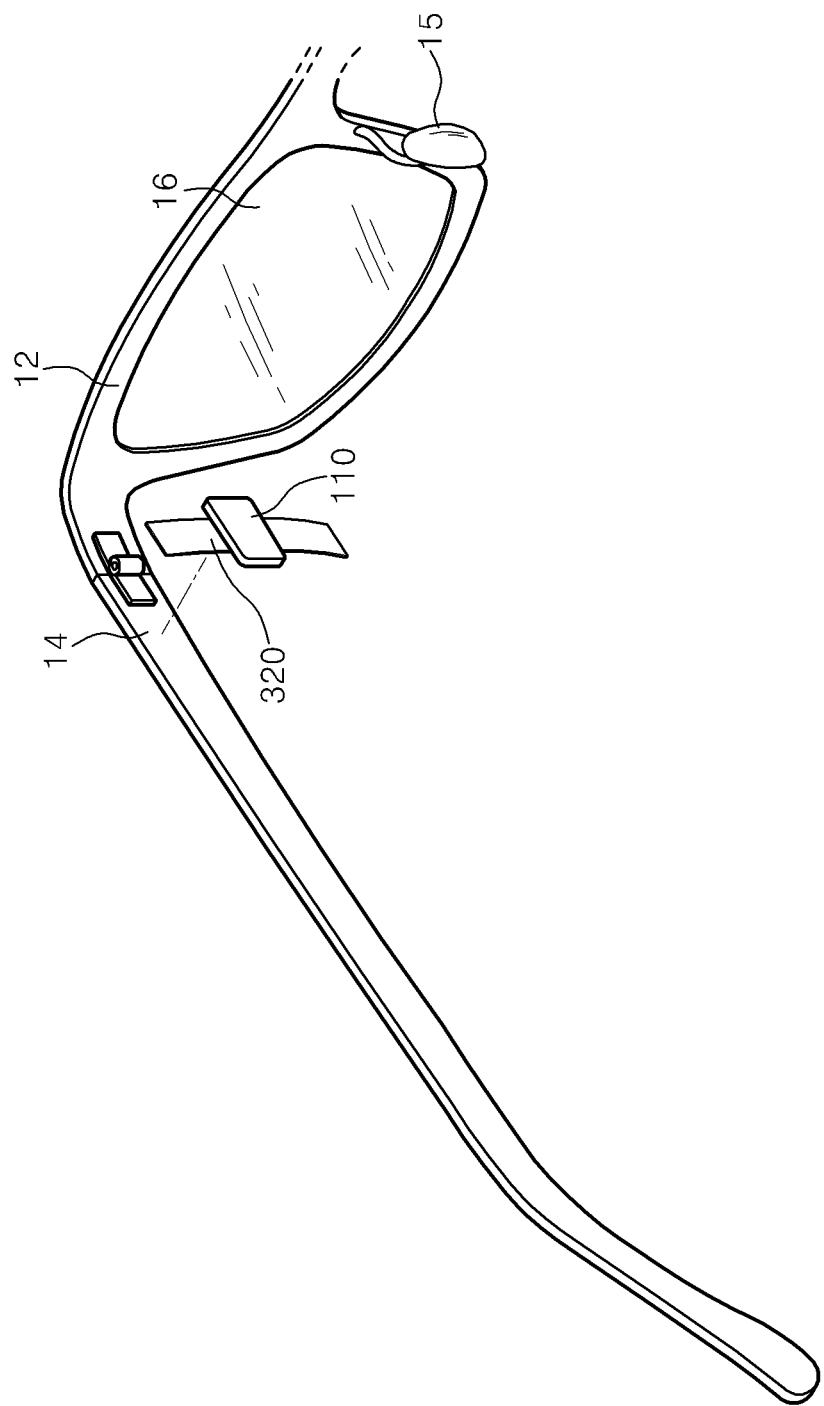
FIG. 11 is a perspective view illustrating a sixth embodiment of a drug carrier device attachable to glasses according to the present invention.
Figure 12:
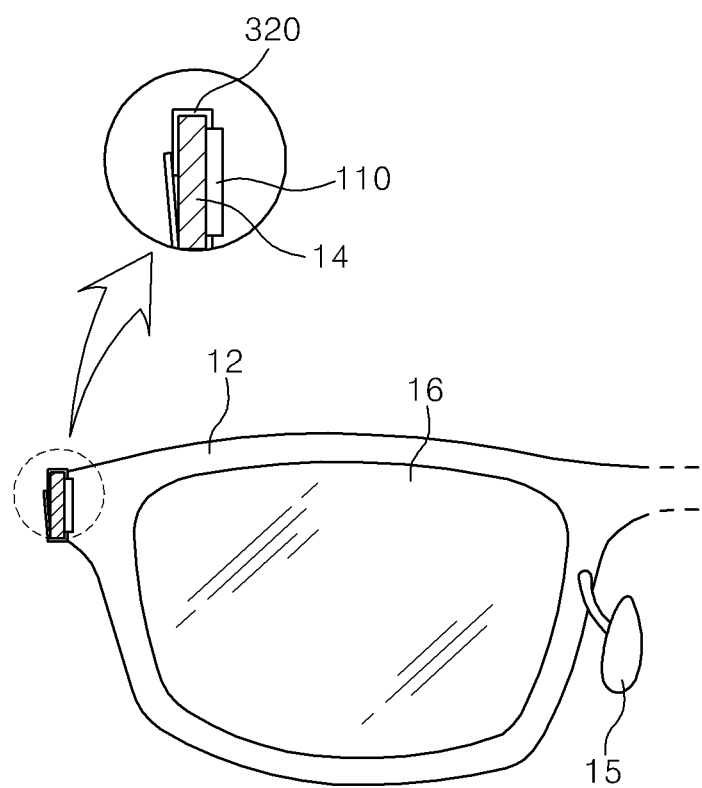
FIG. 12 is a cross-sectional view of FIG. 11.

In the illustrated embodiments, the drug carrier 110 is generally installed to be placed over the lens frames 12. However, as shown in FIGS. 10 to 12, the drug carrier 110 may also be attached to a bow frame 14 through the fixing unit to supply drugs through the skin or mucous membranes.

Figure 10:
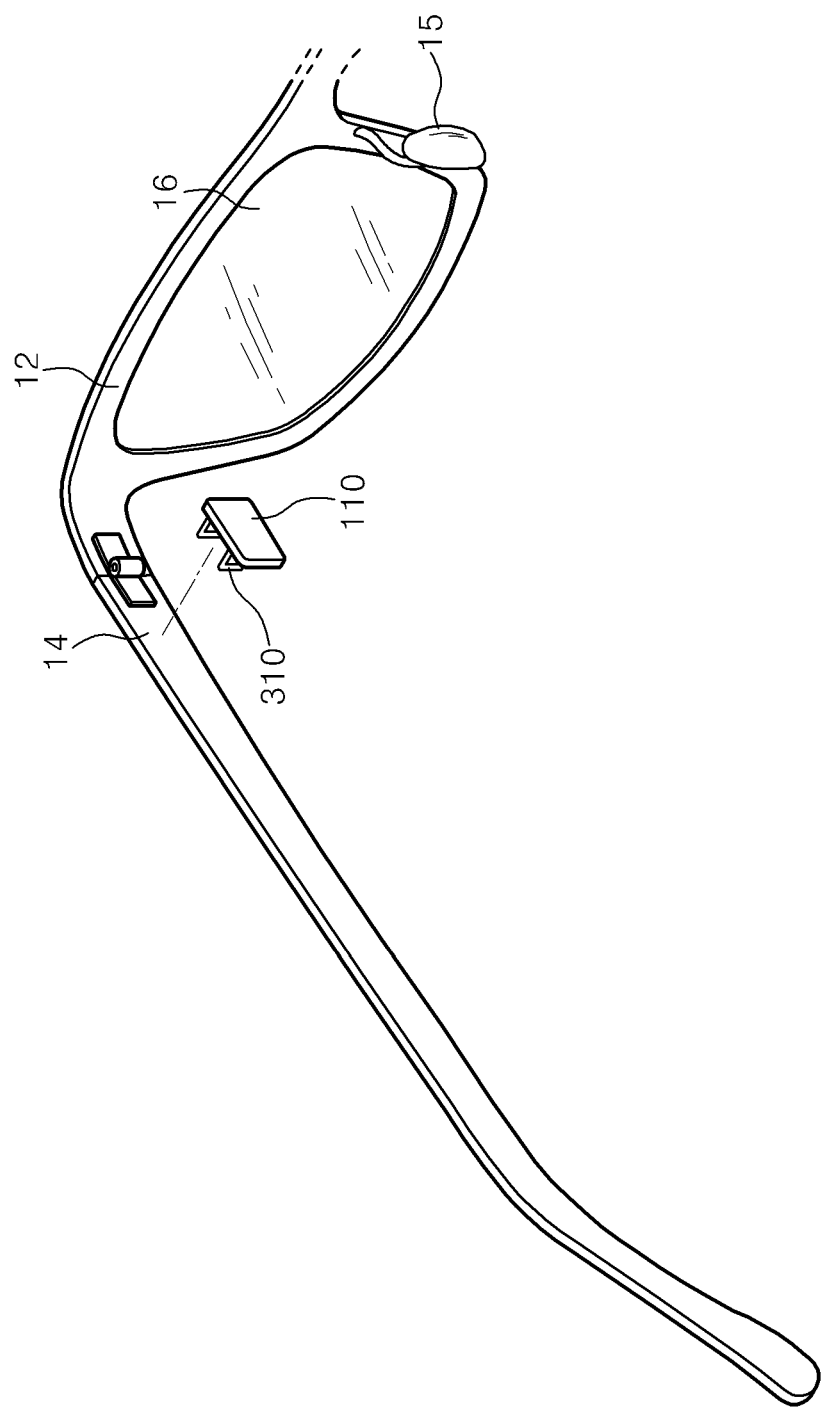
FIG. 10 is a perspective view illustrating a fifth embodiment of a drug carrier device attachable to glasses according to the present invention.

As shown in FIG. 10, a hanger member 310 for fixing the drug carrier 110 on the bow frame 14 may be installed to be mounted on a rising edge of the bow frame 14. The rising edge of the bow frame 14 is positioned in proximity to a lens frame 12 and is close to the eyes when the glasses are worn although it is not directly brought into contact with the facial surface of a wearer. Accordingly, medicinal herb ingredients can be easily released to the eyes.

As the fixing unit for fixing the drug carrier 110 to the bow frame 14, a velcro tape 320 may be employed. Since the drug carrier 110 is fixed to the bow frame 14 through the velcro tape 320 surrounding the bow frame 14 and the velcro tape 320 are easily attachable to or detachable from the drug carrier 110, the drug carrier 110 can be easily replaced.

The drug carrier 110 may be fixed to a bow member of glasses through various fixing units in addition to the aforementioned fixing units.

Figure 13:
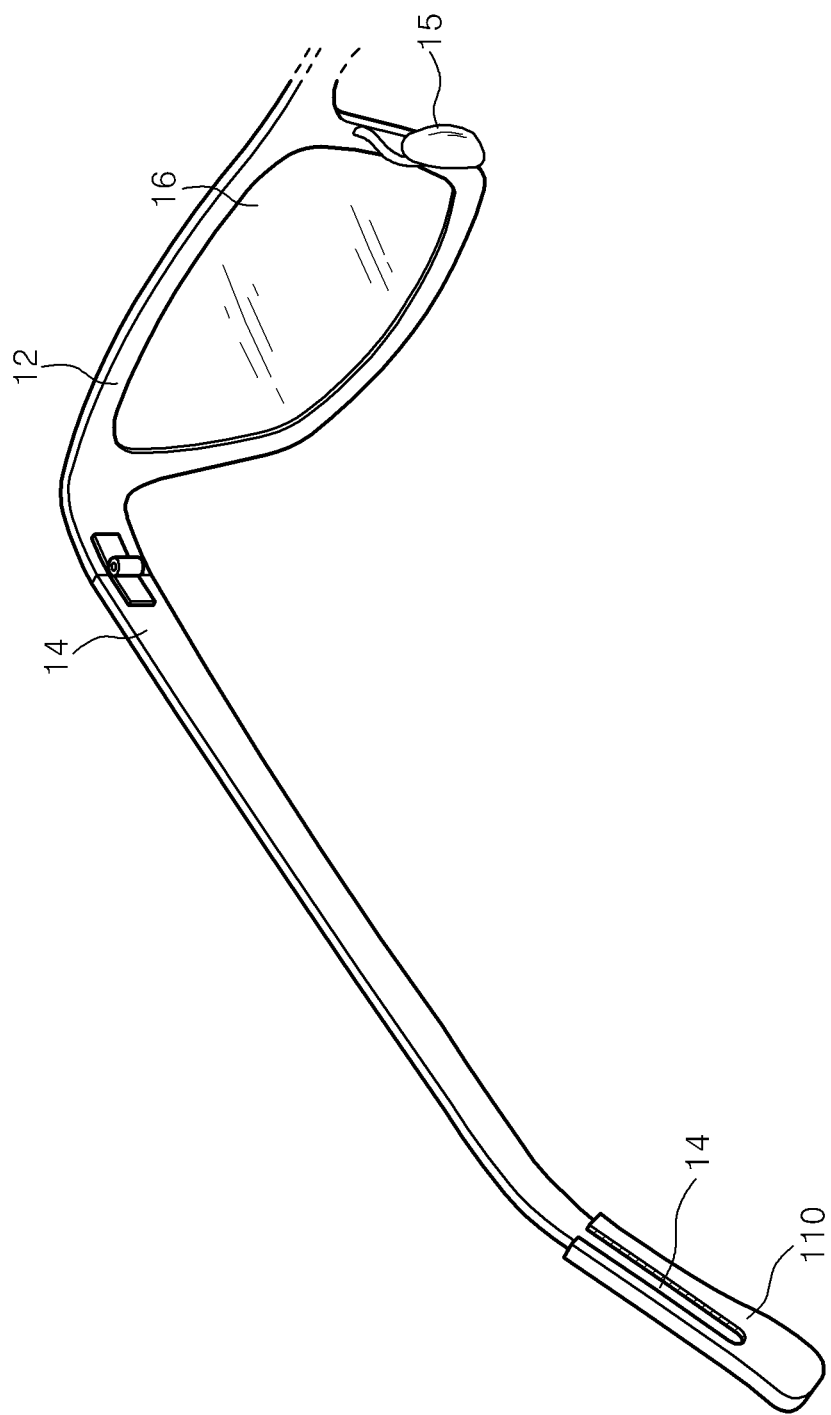
FIG. 13 is a perspective view illustrating a seventh embodiment of a drug carrier device attachable to glasses according to the present invention.

FIG. 13 illustrates that a drug carrier 410 is fastened to a rear end of a bow member 14.

The drug carrier 410 is formed in a bag shape having an insertion groove into which the bow member 14 can be inserted. The drug carrier 410 is mounted to surround an end portion of the bow member 14. Medicinal herb ingredients contained in the drug carrier 110 may penetrate into the interior of the skin through skin mucous membrane behind wearer's ears.

The glasses may be ordinary glasses for correcting a wearer's vision, or a variety of functional glasses specially fabricated to be suited to uses, including welding, experimental use, watching 3D video, and so on. The drug carrier 410 may also have variable shapes according to the types of glasses.

Figure 14:
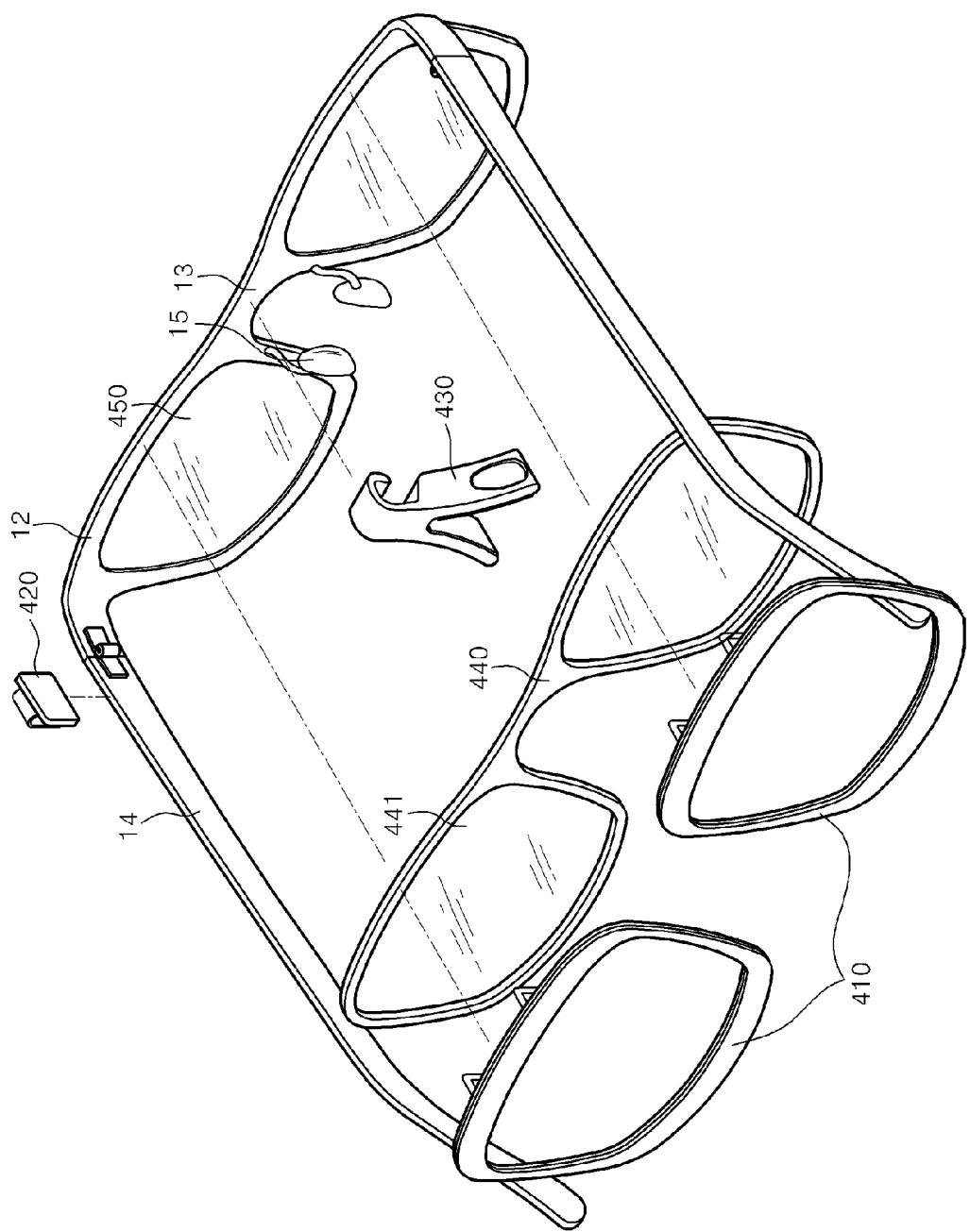
FIG. 14 is an exploded perspective view illustrating a drug carrier device attachable to glasses having a plurality of drug carriers mounted thereon.

FIG. 14 illustrates an embodiment in which multiple drug carriers 410, 420 and 430 are mounted on functional glasses.

That is to say, first to third drug carriers 410, 420 and 430 are installed on a lens frame 12, a connection frame 13 and a bow frame 14, respectively. Since the drug carriers 410, 420 and 430 are substantially the same as the drug carriers of the preceding embodiments.

In the illustrated embodiment, the glasses are used for watching 3D video, and a functional lens 450 is attached to the glasses to perform the function for watching 3D video.

Since the functional lens 450 has no vision corrective function, a correcting lens frame 440 having a correcting lens 441 for correcting a wearer's vision may further be installed in front of the functional lens 450.

In the illustrated embodiment, the correcting lens frame 440 is magnetically coupled to the frame of glasses using a magnet. Alternatively, the correcting lens frame 440 may be installed on the frame of glasses using various coupling mechanisms, including a loop based hanging method, an adhesion method using an adhesive tape or adhesive material, and so on, in addition to the magnet, thereby enabling the wearer to watch 3D video with a corrected vision.

Unlike in the illustrated embodiment, the correcting lens 441 may be installed in front of the functional lens 450. In addition, coupling of the correcting lens frame 440 to the frame of glasses may be implemented using various coupling units.

Figure 15:
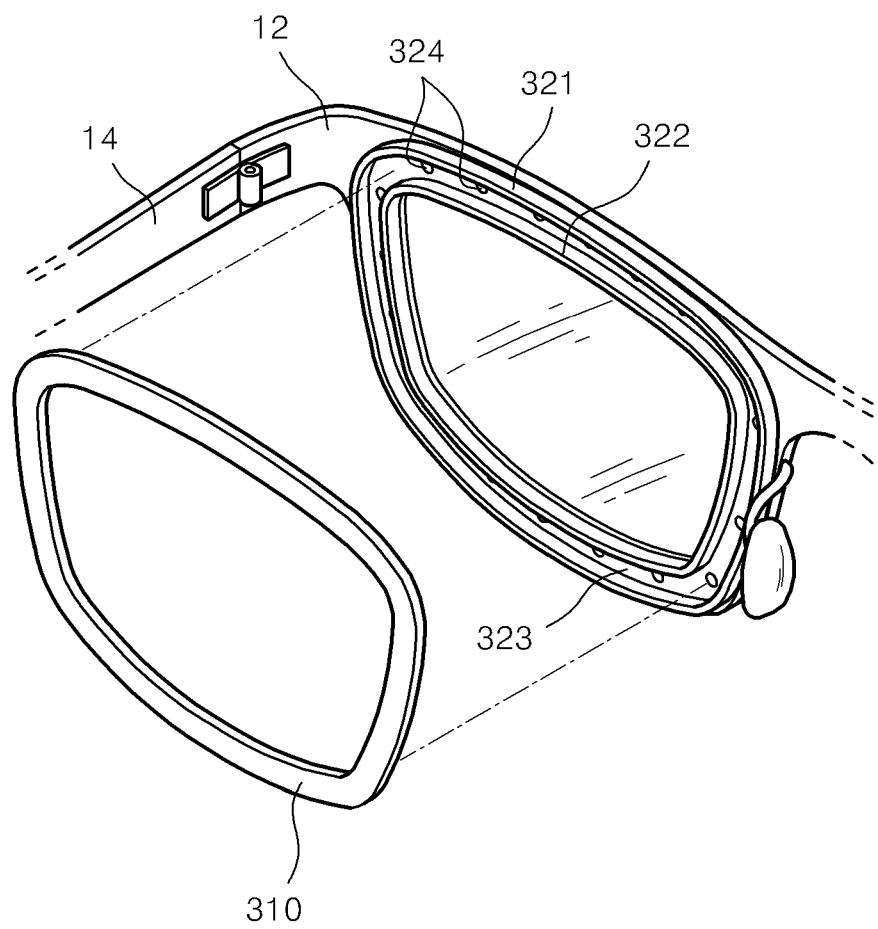
FIG. 15 is a partially cut-away perspective view illustrating another embodiment in which an attaching portion is formed on a lens frame to attach a drug sheet thereto.

FIG. 15 illustrates an embodiment in which a couple of guide units, i.e., first and second guide units 321 and 322, spaced a predetermined distance apart from each other, are provided to attach the drug sheet 310 to the interior of a lens frame 12.

In the illustrated embodiment, an attaching portion 323 is provided between the first and second guide units 321 and 322 to attach the drug sheet 310 by the first and second guide units 321 and 322. A plurality of magnets may be installed on the attaching portion 323.

Figure 16:
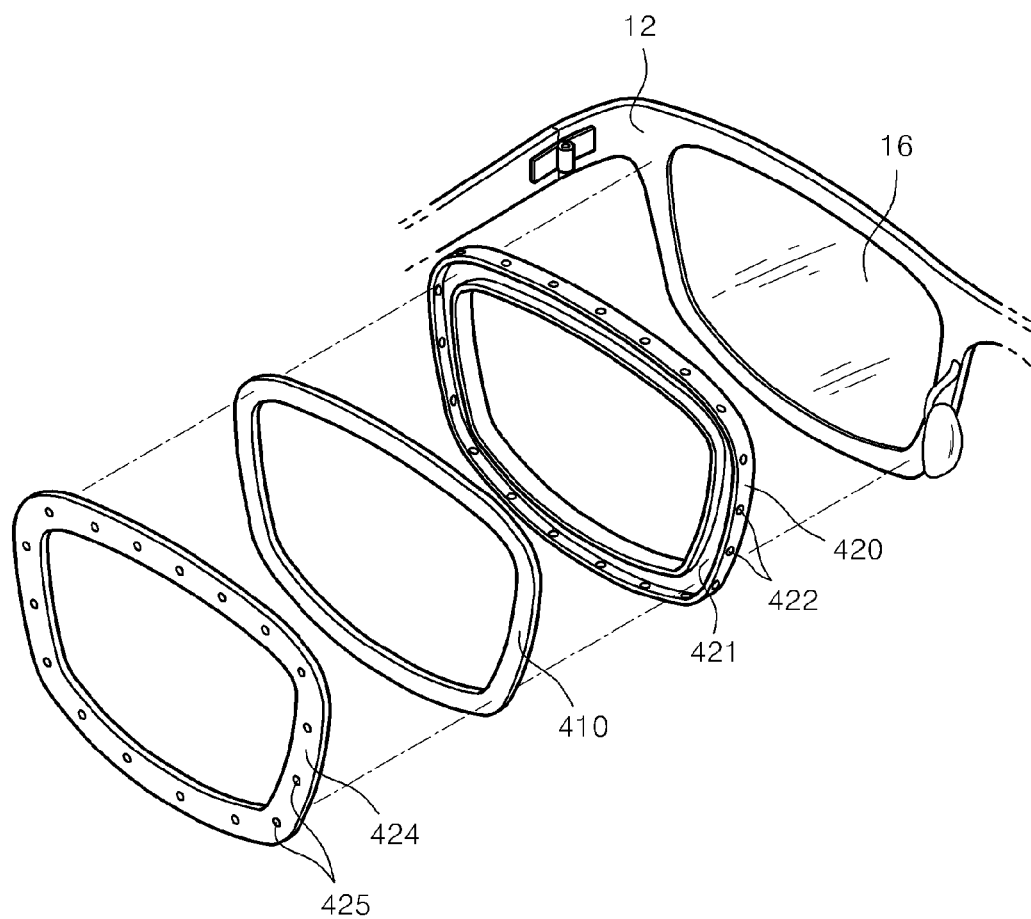
FIG. 16 is a perspective view illustrating an eighth embodiment of a drug carrier device attachable to glasses according to the present invention.

In the embodiment shown in FIG. 16, a base frame 420 is formed to be attached to an internal surface of a lens frame 12 using an adhesive. A receiving groove 421 is formed on a front surface of the base frame 420 to receive the drug sheet 410 and attach the drug sheet 410 thereto, and a cover frame 424 is provided to cover the receiving groove 421.

A plurality of discharge holes 425 are formed in the cover frame 424 to allow medicinal herb ingredients contained in the drug sheet 410 to be discharged. Air holes 422 are formed on lateral surfaces of the base frame 420 to allow air to flow into an inner space of the base frame 420, created by the receiving groove 421.

In the illustrated embodiment, the air easily passes the drug sheet 410 and then moves through the air holes 422 formed in the base frame 420 and the discharge holes 425 formed in the cover frame 424, thereby easily releasing medicinal herb ingredients contained in the drug sheet 410.

In addition, in the illustrated embodiment, although not shown, a covering plate for covering opposite sides of a lens may further be provided in a lens frame or a bow frame, thereby allowing a wearer to stay focused on a screen or a book increasing.

In addition, in the above-described embodiments, the drug carrier according to the present invention is formed as a drug sheet containing medicinal herb ingredients. However, in addition to the drug sheet, the drug carrier may also be in the form of powder, a capsule or a gel containing medicinal herb ingredients. Like in the embodiment shown in FIG. 16, the drug carrier may be configured to fill a space created by a base frame and a cover frame.

Although exemplary embodiments of the present invention have been described in detail hereinabove, it should be understood that many variations and modifications of the basic inventive concept herein described, which may appear to those skilled in the art, will still fall within the spirit and scope of the exemplary embodiments of the present invention as defined by the appended claims.

Since the drug carrier device attachable to glasses according to the present invention can be used in a state in which it is attached to the glasses worn at normal times, utilization of the drug carrier device is increased, so that it can be highly applicable in the industrial fields.

What is claimed is:

1. A drug carrier device attachable to glasses comprising: a drug carrier containing medicinal herb ingredients; and a fixing unit for detachably fixing the drug carrier on a frame of glasses, wherein the drug carrier includes a base frame mounted on the frame of glasses by the fixing unit, a drug sheet detachably installed on the base frame, and a cover frame coupled to the surface of the base frame to which the drug sheet is attached and wherein the cover frame has a plurality of discharge holes to allow the medicinal ingredients of the drug sheet to be discharged, and vent holes communicating with the drug sheet are formed in the base frame to connect the drug sheet with the outside of the drug carrier.

2. The drug carrier device of claim 1, wherein the fixing unit is a fixing loop extending from the drug carrier and has an end portion bent to be hooked on a frame of the glasses.

3. The drug carrier device of claim 1, wherein the frame of the glasses is made of a metal to be magnetically coupled to a magnet and the fixing unit includes a permanent magnet magnetically coupled to the frame of glasses.

4. The drug carrier device of claim 1, wherein the frame of the glasses has a plurality of recessed grooves formed on a surface to which the drug carrier is attached, and the fixing unit includes fixing protrusions protruding from the drug carrier and inserted into the recessed grooves.

5. The drug carrier device of claim 1, wherein the fixing unit is made of an adhesive material coated on a contact surface where the drug carrier and the frame of the glasses are brought into contact with each other.

6. The drug carrier device of claim 1, wherein the base frame includes a magnet member provided on its surface to which the drug sheet is attached to facilitate releasing of medicinal ingredients contained in the drug sheet.

7. The drug carrier device of claim 1, wherein the glasses further include a polarizing lens for watching 3D video or a polarizing lens unit detachably coupled to the frame of the glasses and including a polarizing lens for watching 3D video.

8. The drug carrier device of claim 1, wherein a correcting lens frame including a correcting lens for correcting a wearer's vision is detachably installed to the frame of the glasses.

9. The drug carrier device of claim 1, wherein the drug carrier is in the form of one of powder, a capsule and a gel containing medicinal herb ingredients.

* * * * *